United States Patent [19]

Mitra et al.

[11] Patent Number: 4,470,968
[45] Date of Patent: Sep. 11, 1984

[54] PASTEURIZED THERAPEUTICALLY ACTIVE BLOOD COAGULATION FACTOR CONCENTRATES

[75] Inventors: Gautam Mitra, Kensington; Paul K. Ng, Hercules, both of Calif.

[73] Assignee: Miles Laboratories, Inc., Elkhart, Ind.

[21] Appl. No.: 457,593

[22] Filed: Jan. 13, 1983

[51] Int. Cl.³ ............................................. A61K 35/14
[52] U.S. Cl. .................................................... 424/101
[58] Field of Search ......................................... 424/101

[56] References Cited

U.S. PATENT DOCUMENTS 4,379,085  4/1983  Williams et al. ................... 424/101

Primary Examiner—Sam Rosen
Attorney, Agent, or Firm—Lester E. Johnson; Theodore J. Leitereg

[57] ABSTRACT

Compositions containing a concentrate of coagulation Factors II, VII, IX, and X are pasteurized without substantial loss of therapeutic activity by mixing the protein composition with a pasteurization-stabilizing amount of a polyol and a source of citrate ions prior to pasteurization. Pasteurized compositions containing a concentrate of coagulation Factors II, VII, IX, and X, which have heretofore been unattainable, can be prepared by the method of the invention.

12 Claims, No Drawings

PASTEURIZED THERAPEUTICALLY ACTIVE BLOOD COAGULATION FACTOR CONCENTRATES

BACKGROUND OF THE INVENTION

1. Field of the Invention

This invention relates to and has among its objects the provision of compositions for therapeutic use and methods of making them. It is a particular object of this invention to provide pasteurized compositions containing a concentrate of coagulation Factors II, VII, IX, and X. Further objects of the invention will be evident from the following description wherein parts and percentages are by weight unless otherwise specified.

2. Description of the Prior Art

Many useful blood fractions and blood proteins are obtained from human blood plasma by fractionation according to known techniques such as, for example, the alcohol fractionation method of Cohn described in U.S. Pat. No. 2,390,074 (1945) and the *Journal of the American Chemical Society,* Vol. 68, page 459 (1946) and the Rivanol® ammonium sulfate method. The aforementioned methods as well as other variations and techniques are summarized in "The Plasma Proteins", second edition, Volume III, pages 548–550, Academic Press, New York, NY (1977). These blood fractions contain biologically active proteins that possess certain therapeutic qualities. For instance, a concentrate of Factors II, VII, IX and X is useful in treating individuals who have hemophilia. There are estimated to be 100,000 cases of congenital hemophilia in the U.S. Of these, approximately 20,000 are cases of hemophilia B, the blood of such patients being either totally devoid of plasma thromboplastin component or seriously deficient in plasma thromboplastin component. The disease therefore exists in varying degrees of severity, requiring therapy anywhere from every week up to once or twice a year. The completely deficient cases require replacement therapy once every week; the partially deficient cases require therapy only when bleeding episodes occur, which may be as seldom as once a year. The bleeding episodes in congenital, partially-deficient cases are generally caused by a temporarily acquired susceptibility rather than by injury alone. Intravenous injection of a sufficiently large amount of fresh plasma, or an equivalent amount of fresh blood, temporarily corrects the defect of a deficient subject. The beneficial effect often lasts for two or three weeks, although the coagulation defect as measured by in-vitro tests on the patient's blood appears improved for only two or three days. Such therapy with fresh plasma or fresh blood is effective but it has several serious drawbacks: (1) it requires ready availability of a large amount of fresh plasma; (2) requires hospitalization for the administration of the plasma; (3) a great many of the patients become sensitized to repeated blood or plasma infusions and ultimately encounter fatal transfusion reactions; (4) at best plasma can only partially alleviate the deficiency; and (5) prolonged treatment or surgery is not possible because the large amounts of blood or plasma which are required will cause acute and fatal edema.

Because of the above, concentrates of coagulation Factors II, VII, IX, and X (Factors IX concentrates) have been developed for administration to hemophilia B patients (for example, the concentrate of Factors II, VII, IX, and X disclosed in U.S. Pat. No. 3,717,708).

One problem confronting users of Factor IX concentrates is the thermal instability of the therapeutically active proteins contained therein. In many cases, substantial, and sometimes complete, losses of activity are observed if these concentrates are heated above physiologically compatible temperatures, i.e., above about 40°–45° C. Consequently, these items require special care during preparation and storage to minimize such deactivation.

The thermal instability of the aforementioned proteins renders them unpasteurizable. Therapeutically active proteins isolated from plasma may contain viruses, e.g., hepatitis virus, present in the source material for the protein fraction, namely, blood from a donor. A risk of contracting hepatitis exists, therefore, for those receiving unpasteurized fractions from blood plasma fractionation because the presence of the virus cannot be detected with certainty by any known procedure. In a large number of situations, this risk is outweighed by the detriment to a patient in not receiving the therapeutic plasma fraction as determined by the physician.

Some therapeutically active proteins derived from plasma have been pasteurized successfully. For example, it is well known that albumin can be pasteurized by heating at 60° C. or 64° C. for 10 hours (Gellis et al, *J. Clin. Invest.,* Vol. 27, pages 239–244 [1948]) in the presence of certain stabilizers such as acetyl-tryptophan and sodium caprylate. Individuals receiving this pasteurized material did not contract hepatitis, thus indicating the inactivation of hepatitis virus while retaining the activity of albumin under the afore-described heating conditions. Plasma Protein Fraction (human) is also stabilized during pasteurization by the above method.

A process for pasteurizing plasminogen is disclosed by Baumgarten et al in U.S. Pat. No. 3,227,626. An aqueous preparation containing 0.25–20 milligrams per milliliter (mg/ml) of plasminogen and further containing 0.1–0.5 molar lysine with a pH of 5.3–7.5 was heated at 60° C. for 10 hours. As the patentee states, hepatitis virus was destroyed and the danger of transmitting hepatitis was removed with retention of plasminogen activity. Attempts to pasteurize plasminogen under the above conditions in the absence of lysine resulted in complete destruction of plasminogen activity. It is interesting to note that plasminogen cannot be stabilized with N-acetyl-tryptophan and sodium caprylate during pasteurization, nor can albumin and Plasma Protein Fraction (human) be pasteurized in the presence of lysine.

Singher has described a process for treating plasminogen to produce a material that is not contaminated with hepatitis virus (U.S. Pat. No. 2,897,123). In the patented pasteurization technique aqueous solutions of plasminogen are heated at about 60° C. for about 10 hours. The activity of plasminogen is retained if the solutions have a pH in the range not less than 3 nor greater than 6.5 and an ionic strength not greater than 0.2.

Another method for removing hepatitis virus from a biological material is described in U.S. Pat. No. 4,168,300. The material to be treated is contacted with a preparation, which may be agarose gel or beaded polyacrylamide plastic coupled with a variety of hydrophobic ligands. Plasma and albumin were subjected to the above purification technique to remove hepatitis virus.

Aqueous solutions of the enzyme thrombin have been stabilized (Seegers, *Arch. Biochem.,* 1944, Vol. 3, pages 363–367) during heating at 50° C. in the presence of saturation amounts of certain glycosides. The stabilized solutions were heated at the above temperature for a period of 48 hours or more with minimal loss of activity. On the other hand, Seegers also discloses that glycosides and polyols have only minimal effectiveness in stabilizing the enzyme prothrombin. The reversible denaturation of lysozyme and ribonuclease was studied by Gerlsma et al, *Int. J. Peptide Protein Res.*, Vol. 4, pages 377-383 (1972). The authors found that certain polyhydric alcohols increased somewhat the temperatures at which these enzymes were denatured. Finally, Simpson et al, in *J. Am. Chem. Soc.*, Vol. 75, No. 21, pages 5139-5152 (1953) and Donovan in *J. Sci. Fd. Agric.*, Vol. 28, pages 571-578 (1977) noted that the denaturation temperature of ovalbumin (an egg white protein) was raised slightly in the presence of sucrose in aqueous solutions of the protein. However, Donovan points out that the temperatures of denaturation of ovalbumin and S-ovalbumin are 84.5° C. and 92.5° C., respectively. Furthermore, ovalbumin and S-ovalbumin, as well as the aforementioned enzymes, have no therapeutic activity in treating disorders in humans, whereas blood plasma proteins are therapeutically active. In fact, as mentioned below, proteolytic enzymes deactivate blood plasma proteins.

Singher, in the aforementioned U.S. patent, lists some methods of destroying hepatitis virus. The least effective of these methods involves the use of either nitrogen mustard or beta-propiolactone. High energy irradiation in appropriate dosage is effective but destroys biological activity when applied to human blood products. Heat is recognized also as effective against hepatitis virus, the preferred treatment being heating the material at 60° C. for 10 hours. Higher temperatures above 70° C. for shorter intervals or lower temperatures for longer intervals have also been tried with successful results. However, it is important to note that higher temperatures are undesirable because of the potential for denaturation of the proteins. Furthermore, lower temperatures for long intervals are to be avoided because various proteolytic enzymes are activated under these conditions, and these activated enzymes cause protein degradation. Also, the use of temperatures lower than 60° C. for pasteurization has not been shown to consistently yield a material that does not contain the infective virus.

As mentioned above, the recognition that heating at 60° C. and 64° C. for 10 hours successfully destroys the hepatitis virus in albumin was made by Gellis et al, supra. Gellis et al proved experimentally that albumin heated under the above conditions did not transmit hepatitis even if hepatitis virus was present prior to pasteurization. However, the author noted that hepatitis virus survived heating at 56° C. for one hour, a temperature usually employed for the inactivation of viruses. Thus, although heating at temperatures of about 56° C. for one hour will deactivate most viruses, hepatitis virus is not inactivated; and materials containing hepatitis virus, which are heated at 56° C. for one hour, cause infection of hepatitis in individuals receiving such materials.

Japanese Pat. No. 51-134878 (1976) teaches the stabilization of Factor XIII against heat inactivation (60° C. for 10 hours) by using 10-20% (w/v) of a stabilizer such as a neutral amino acid, a monosaccharide, or a sugar alcohol. Furthermore, in U.S. Pat. No. 4,297,344 there is disclosed a method of stabilizing coagulation Factors II, VIII, XIII, antithrombin III, and plasminogen against heat in the presence of a 1-3 molar amount of a certain amino acid and 20-60% (w/w) of a carbohydrate. Haptoglobin has been pasteurized in the presence of a stabilizer such as an amino acid, a mono- or di-saccharide or a sugar alcohol.

In German Offenlegungsschrift No. 3043857 there is disclosed a method for the manufacture of a hepatitis-free preparation of coagulation Factors II and/or VII. The method is characterized by mixing the preparation of Factor II and/or VII with an amino acid and/or a saccharide or sugar alcohol and a chelating agent such as ethylene diamine tetraacetate or theylene glycol-bis-(2-aminoethylene either)-tetracetate and heating the mixture to inactivate hepatitis virus.

Antithrombin compositions have been mixed with citrate ions in order to stabilize the antithrombin to heat. (Holleman et al, *Thromb. Haemostasis*, 38, 201 [1977]).

SUMMARY OF THE INVETNION

The invention described herein provides means for obviating the above-outlined problems. In the method of the invention compositions containing a concentrate of coagulation Factors II, VII, IX, and X are rendered heat stable during pasteurization or heating at a temperature of about 60°-100° C. by mixing with heat-stabilizing or pasteurization-stabilizing amounts of a polyol and a source of citrate ions. Pasteurized compositions containing a concentrate of coagulation Factors II, VII, IX, and X heretofore unobtainable are available as a result of the process of our invention by heating a mixture of unpasteurized protein composition, a polyol, and a source of citrate ions suspended or solubilized usually in an aqueous medium at a temperature and for a time sufficient to pasteurize the protein composition. Following pasteurization or heat treatment, the polyol and citrate ions are removed totally or in part, as desired, from the protein composition by conventional techniques, and the pasteurized protein composition is processed according to conventional procedures for its ultimate therapeutic use.

The primary advantage of the invention is the availability of thermally stable and pasteurized compositions comprising a concentrate of coagulation Factors II, VII, IX, and X, which heretofore have been unknown and unattainable. Since the therapeutically active protein compositions of the invention can be heated with minimal loss of activity under conditions known to inactivate hepatitis virus, these valuable materials can be administered to patients, who can obtain the full therapeutic benefits thereof with a substantially reduced risk of being infected by hepatitis virus.

DESCRIPTION OF THE PREFERRED EMBODIMENTS

As mentioned above, the products of the invention include pasteurized or heat-treated compositions comprising a concentrate of coagulation Factors II, VII, IX, and X, which have been subjected to pasteurization or heating at temperatures of about 60°-100° C., preferably about 60°-75° C. when mixed with thermal-stabilizing or pasteurization-stabilizing amounts of a polyol and a source of citrate ions, the pasteurized compositions containing or being free of polyol and citrate ions.

The starting material for the process of this invention is an unpasteurized composition comprising a concentrate of coagulation Factors II, VII, IX, and X which composition could be hepatitis infective, i.e., could contain infective amounts of hepatitis virus. Concentrates of Factors II, VII, IX, and X (Factor IX concentrate prothrombin complex) may be obtained from blood plasma in a number of ways. By way of illustration and not limitation, one may employ the method of U.S. Pat. No, 3,717,708 (herein incorporated by reference) or any of the methods of the prior art described therein. In the method of U.S. Pat. No. 3,717,708 Cohn Supernatant I, Method 6 from unmodified citrated human plasma is applied to an ion exchange resin on to which the coagulation Factors II, VII, IX, and X are adsorbed. The above-mentioned factors are then selectively eluted from the ion exchange resin. Exemplary of another method for preparing a Factor IX concentrate is a process described in U.S. Pat. No. 4,272,523. In general, Factor IX concentrates from human blood plasma are suspect for being hepatitis infective.

The Factor IX composition generally contains about 1–20% by weight of the coagulation Factors, usually at least about 5% by weight. The coagulant activities in general are normally present in the composition in the following ratio: Factor II:Factor IX of about 0–10, preferably about 0.1–2.0, Factor VII:Factor IX of about 0–10, preferably about 0.1–2.0, and Factor X:Factor IX of about 0–10, preferably about 0.1–2.0.

In the method of the invention, the protein composition to be pasteurized is suspended or dissolved in an aqueous medium with an amount of polyol and a source of citrate ions sufficient to stabilize the protein composition during subsequent pasteurization. The concentration of polyol and citrate ions necessary to stabilize a protein composition in accordance with this invention depends on the concentration of therapeutically active protein in the protein composition and on the type of polyol. Generally, the thermal-stabilizing amount or pasteurization-stabilizing amount of polyol should be within the range of about 1–1000 parts, preferably 5–100 parts, of polyol per part of total protein in the protein composition. Generally, about one part of protein composition is mixed with about 1–500 parts, preferably 4–200 parts, of an aqueous medium containing at least about 20%, preferably at least about 30%, to saturation, preferably at the temperature of pasteurization, of polyol, on a weight to volume basis. The therapeutically active protein is considered to be stabilized if it retains a substantial portion, i.e., at least 40%, of its therapeutic activity during pasteurization. It is preferred that 50% or more of the therapeutic activity of the Factor IX concentrate be retained during pasteurization. Consequently, the amount of polyol to be added should be such as to retain the above-recited amount of therapeutic activity.

The amount of citrate ions usually is about 0.1–1.0 moles per liter of solution, preferably about 0.3–0.5 moles per liter.

After the protein composition has been mixed with the polyol and citrate ions, the mixture is heated at a temperature and for a time sufficient to pasteurize it.

Thus, the mixture is pasteurized upon heating it under conditions known to inactivate hepatitis virus. Effective pasteurization to inactivate hepatitis virus and to substantially reduce the risk of hepatitis infection is obtained by heating an unpasteurized protein composition at a temperature of about 60–100° C., preferably about 60–75° C. for a period of about 1–10 hours, preferably 6–10 hours, usually about 60–65° C. for about 10 hours.

The pasteurization is carried out under pH conditions which are physiologically acceptable. Thus, the pH of the mixture usually should be within the range of about 5.5–8.0, preferably about 6.0–7.5. In general, physiological conditions are desirable, where possible, during pasteurization to insure the least disturbance to the therapeutically active protein composition.

The amount of a particular polyol and of citrate ions required to stabilize a specific protein composition during pasteurization and the conditions necessary to pasteurize the composition can be determined readily by one skilled in the art using pilot trials in accordance with the teaching contained herein.

Following pasteurization the mixture of polyol, citrate ions and protein composition may be treated to remove all or part of the polyol and citrate ions. Conventional techniques can be employed to achieve this end. For example, the mixture can be dialyzed or diafiltered using an appropriate semi-permeable membrane. Other means of removing the polyol and citrate ions will be suggested to those skilled in the art.

The pasteurized mixture may be treated to remove water therefrom by procedures well known in the art. For instance, the mixture can be freeze-dried or ultrafiltered and then freeze-dried. Furthermore, the mixture can be sterile-filtered by conventional methods prior to water removal.

The pasteurized protein compositions of the invention can be formulated into pharmaceutical preparations for therapeutic use. To prepare it for intravenous administration the protein composition is dissolved usually in water containing physiological substances such as sodium chloride, glycine, and the like and having a buffered pH compatible with physiological conditions. Generally, guidelines for intravenously administered protein compositions are established by governmental regulation.

The term "polyol" means a substance with more than one hydroxyl group (—OH) and includes polyhydric alcohols and carbohydrates such as sugars. It is preferred that the polyol be water miscible, physiologically acceptable if infused, physically compatible with the protein, and have a low molecular weight, i.e., a molecular weight less than about 5000. Higher molecular weight polyols, e.g., polysaccharides such as dextrin, starch, glycogen, cellulose, pentosans, pectin, hemicellulose, and the like, are not preferred for use in the present method because they are generally water immiscible and are difficult to separate from the protein composition after pasteurization has been completed.

Typical examples of sugars that may be employed in our method are mono-, di-, and trisaccharides such as arabinose, glucose, galactose, fructose, ribose, mannose, rhamnose, sucrose, maltose, raffinose, melezitose, and so forth. Exemplary of polyhydric alcohols or reduced sugars, included with in the purview of the invention are erythritol, ribitol, sylitol, sorbitol, mannitol, etc.

Also within the compass of the invention are mixtures of polyols and substances that produce a polyol in the presence of water or heat such as hydrates, actonides, or the like.

As the source of citrate ions one may use sodium citrate, potassium citrate, and so forth.

It is advantageous in conducting the pasteurization of the invention that the ionic strength of the pasteurization mixture should be physiologically compatible, usually about 0.05–0.2. To this end a salt such as sodium chloride or the like may be added to or removed from the pasteurization mixture to achieve the desired ionic strength.

The method of the invention may be used also in conjunction with other methods for inactivating hepatitis virus such as pasteurizing protein compositions in the presence of other stabilizers such as amino acids or heating protein compositions in the presence of substances known to kill hepatitis virus.

As the amino acid one may employ lysine, arginine, leucine, iso-leucine, methionine, phenylalanine, threonine, tryptophan, valine, alanine, aspartic acid, cysteine, glutamic acid, glycine, histidine, proline, serine, tyrosine, and the like. Substances producing the aforesaid amino acids such as an amino acid salt and the like also may be used. It should be understood that amino acids in the absence of a polyol are not effective pasteurization-stabilizing agents for Factor IX concentrates.

As mentioned above the pasteurized compositions of the invention comprising a Factor IX concentrate may be incorporated into pharmaceutical preparations, which may be used for therapeutic purposes. However, the term "pharmaceutical preparation" is intended in a broader sense herein to include preparations containing a protein composition pasteurized in accordance with this invention used not only for therapeutic purposes, but also for reagent purposes as known in the art; for tissue culture wherein organisms such as viruses for the production of vaccines, interferon, and the like, are grown on plasma or on plasma fractions, e.g., Cohn Effluent II+III, Cohn Fraction IV, Cohn Fraction V, and so forth; etc.

For any of the above uses it is advantageous that the protein composition be free of infective hepatitis as provided in the instant invention. The pharmaceutical preparation intended for therapeutic use should contain a therapeutic amount of a pasteurized protein composition, i.e., that amount necessary for preventative or curative health measures. If the pharmaceutical preparation is to be employed as a reagent, then it should contain reagent amounts of pasteurized protein composition. Similarly, when used in tissue culture or a culture medium the pasteurized protein composition should contain an amount of protein composition sufficient to obtain the desired growth. It should be obvious that protein compositions pasteurized in accordance with this invention will not contain infective amounts of viruses and other organisms which are inactivated under the pasteurization conditions.

The invention described above is demonstrated further by the following illustrative examples.

EXAMPLES

Assay Methods

Factors II and VII: Factor II and Factor VII were assayed by the method of Owren described in the *Scand. J. Clin. and Lab. Investigation,* Vol. 1, page 81 (1949).

Factors X and Xa: Factor X and Factor Xa were assayed by the method of Bachmen et al, described in *Thromb. Diath. Haemorrh.,* Vol. 2, page 24, (1958).

Thrombin: The assay procedure employed was described by Fenton II et al, in *Thrombosis Res.,* Vol. 4, pages 809–817 (1974).

Factors IX and VIII: Modification of the procedures described by Langdell et al (partial thromboplastin time technique), *J. Lab. Clin. Med.,* Vol. 41, pages 637–647 (1953) and by Proctor et al (kaolin clotting time method) *Amer. J. Clin. Path.,* Vol. 36, page 212 (1961) were employed. Platelet Factor 3 was supplied by a cephalin suspension. Maximum surface contact activation was achieved with Celite ® powder. All other clotting factors (except Factor IX or Factor VIII) were supplied by a substrate comprising plasma from a patient severely deficient in Factor IX or Factor VIII mixed with barium sulfate adsorbed beef plasma. Quantitation of an unknown specimen was made by comparing its clotting time in the test with that achieved by dilutions of a normal standard.

The exact assay procedure is the same for both Factor IX and Factor VIII except that the activator in Factor IX assay is Platelin ® Plus Activator instead of automated APTT reagent (General Diagnostics, Inc., Morris Plains, N.J.).

Non-Activated Partial Thromboplastin Time (NAPTT): A 0.1-ml sample of NAPTT Substrate Plasma (stored on ice), a 0.1-ml sample of Partial Thromboplastin with no activator (stored on ice), and 0.1-ml of the sample to be tested (in various dilutions) were added to a 10×75 mm polystyrene test tube, mixed by shaking carefully and placed in 37° C. water bath with simultaneous starting of a stopwatch. After exactly a one-minute period, 0.1 ml 0.025M $CaCl_2$ maintained at 37° C. was added with simultaneous starting of the timer and the contents of the tube were mixed by careful shaking. Thereafter, the tube was held undisturbed for 30 seconds to 1 minute, depending upon the type of sample. It was then tilted from time to time until gelation started or a clot was observed with care being taken to minimize exposure to room temperature which was below 37° C. Time was recorded at the first sign of a clot formation. Development of opacity and gelation preceded the formation of a firm clot.

When the sample was replaced by Tris buffer, NAPTT blank time was obtained. If the blank time was over 300 seconds, the assay was continued. Any substrate plasma which gave a blank time of less than 300 seconds was unacceptable for this test.

By obtaining NAPTT times at a wide range of dilutions and plotting times in seconds on ordinate and dilutions on abscissa, a straight line relation was obtained. In most prothrombin complex (Factor IX) concentrates, inhibitory effect was observed at low dilutions. Therefore, a straight line relationship was observed at 1:100 and higher dilutions. By using a suitable standard such as Factor IX-1 (FN-1) of the Bureau of Biologics and assigning 100 units per ml for this standard, it was possible to construct a standard curve. On this standard curve, the NAPTT times of a given sample were read and expressed as units. Longer NAPTT times (close to blank time) expressed as low NAPTT units/ml indicate reduced thrombogenicity.

EXAMPLE 1

Effluent I (3000 liters) was contacted with 30 kg of DEAE Sephadex gel and mixed together for about one hour at 1–3° C. The mixture was filtered to give 30 kg of gel, 2 kg of which was washed sequentially with 10 liters of 0.2 M ammonium bicarbonate, 10 liters of 0.3 M ammonium bicarbonate and 6 liters of 0.2 M sodium chloride buffer. Elution was carried out with 4 liters of 0.55 M sodium chloride to obtain a protein solution of $A_{280}=10.12$.

The ionic strength of the eluate was reduced four fold by adding three parts of water-for-injection. The solution was ultrafiltered to an $A_{280}$ of 12, after which sodium citrate was added to a level of 0.5 M, pH adjusted to 6.5, and sucrose to a level of 1.2 gm/ml. The mixture was heated at 60° C. for a period of 6 or 10 hours and, after cooling, was combined with an equal volume of 0.09 M NaCl and 0.01 M sodium citrate at pH 7.4 and 5° C. This mixture was diafiltered against not less than 3 volumes of 0.09 M NaCl, 0.01 M sodium citrate, pH 7.4 buffer. Then, the solution was ultrafiltered to a final potency of approximately 25–30 units of Factor IX per ml and the pH adjusted 6.9±0.5.

TABLE 1

| Sample | Coagulation Factors (U/ml) | | | | Specific activity $(U/A_{280})^a$ | NAPTT | |
|---|---|---|---|---|---|---|---|
| | II | VII | IX | X | | $(sec)^b$ | $(sec)^c$ |
| Pasteurized 6 hrs. in accordance with invention | 27.6 | 7.1 | 21.5 | 49.6 | 0.67 | 265 | 293 |
| Pasteurized 10 hrs. in accordance with invention | 30.3 | 6.2 | 20.9 | 59.1 | 0.52 | 242 | 286 |
| Starting Material | 12.2 | 4.0 | 13.6 | 24.8 | 1.13 | 289 | 331 |

$^a$Units IX per $A_{280}$
$^b$1:100 dilution
$^c$1:200 dilution

EXAMPLE 2

Effluent I (1500 liters) was contacted with 15 kg of DEAE Sephadex gel and mixed together for about one hour at 1°–3° C. The mixture was filtered to give 15 kg of gel, which was washed sequentially with 50 liters of 0.2 M ammonium bicarbonate, 50 liters of 0.3 M ammonium bicarbonate. The Factor IX complex was eluted with 0.75 M ammonium bicarbonate until the $A_{280}$ of the eluate drops to approximately 3.5. Ammonium bicarbonate in the eluate was removed by diafiltering against NLT 5 volumes of 0.09 M NaCl, 0.01 M Na citrate pH 7.4. To the solution ($A_{280}=13$) was added sodium cirate to a level of 0.5 M, pH adjusted to 6.5, and sucrose to a level of 1.2 gm/ml. The solution was processed further as in Example 1. The results are summarized below.

TABLE 2

| Sample | Coagulation Factors (U/ml) | | | | Specific activity $(U/A_{280})^a$ | NAPTT | |
|---|---|---|---|---|---|---|---|
| | II | VII | IX | X | | $(sec)^b$ | $(sec)^c$ |
| Pasteurized 10 hrs. in accordance with invention | 25.6 | 12.2 | 17.8 | 37.6 | 0.49 | 250 | 294 |
| Starting Material | 13.0 | 5.0 | 14.8 | 22.3 | 1.14 | 266 | 288 |

$^a$Units IX per $A_{280}$
$^b$1:100 dilution
$^c$1:200 dilution

EXAMPLE 3

The procedure of Example 1 was repeated up to the step of pasteurization at 60° C. for 10 hours. The post pasteurized solution was diluted with two parts of water-for-injection and the pH adjusted to 7.1. The mixture was applied to a DEAE-Sepharose column previously equilibrated in 0.14 M NaCl, 0.005 M phosphate pH 7.1.

The adsorbed Factor IX complex was eluted with a NaCl gradient, 0.14 M - 0.44 M. Fractions containing Factor IX activity were pooled. Specific activities of Factor II, VII, IX and X were 2.5, <0.1, 1.3, and 2.5 respectively.

Having thus described the invention, what is claimed is:

1. A method for pasteurizing a composition comprising coagulation Factors II, VII, IX, and X, which comprises (a) mixing the composition with a polyol selected from suctose or reduced sugars and a source of citrate ions in an aqueous medium, said polyol and citrate ions being present in an amount sufficient to stablilize the protein during pasteurization, and (b) heating the mixture at a temperature and for a time sufficient to pasteurize the composition.

2. The method of claim 1 wherein the composition is mixed with an aqueous solution wherein the amount of polyol and citrate ions in the mixture of Step a is respectively about 20% to saturation of polyol, on a weight to volume basis, and about 0.1–1.0 moles of citrate ion per liter of solution.

3. The method of claim 1 wherein the amounts of polyol and citrate ions is to result in the retention of at least about 40% of the activity of the coagulation Factors II, VII, IX and X during pasteurization of the composition.

4. The method of claim 1 wherein the mixture is heated in Step b at a temperature of about 60°–100° C.

5. The method of claim 1 wherein the mixture is heated for a period of about 1–10 hours.

6. The method of claim 1 which further includes the step of removing the polyol and citrate ions from the mixture of Step b.

7. The method of claim 6 wherein the polyol and citrate ions are removed from the mixture of Step b by subjecting the mixture to diafiltration.

8. The method of claim 6 wherein the polyol and citrate ions are removed from the mixture of Step b by subjecting the mixture to dialysis or ion exchange chromatography.

9. The method of claim 6 which further includes the step of subjecting the composition to sterile filtration.

10. A method of preparing a pasteurized, sterilized concentrate of coagulation Factors II, VII, IX and X, which comprises
(a) mixing the concentrate with a polyol selected from sucrose or reduced sugars and a source of citrate ions in an aqueous medium, said polyol being present in the mixture in an amount of about 30% to saturation, on a weight to volume basis and said citrate ions being present in the mixture in an amount of about 0.1–1.0 moles per liter,
(b) heating the mixture at a temperature of about 60°–100° C. and a pH of about 5.5–8.0 for a time sufficient to pasteurize the concentrate and render it substantially free of infective hepatitis,
(c) removing the polyol and citrate ions from the mixture, and
(d) sterilizing the mixture.

11. The method of claim 10 wherein the mixture is heated in Step b for a period of about 6–10 hours.

12. The method of claim 10 which further includes the step of removing water from the mixture of Step b.

* * * * *